(12) United States Patent
Reijnen

(10) Patent No.: US 12,714,586 B2
(45) Date of Patent: Aug. 25, 2026

(54) BIFURCATED BALLOON EXPANDABLE STENT ASSEMBLY

(71) Applicant: Bentley InnoMed GmbH, Hechingen (DE)

(72) Inventor: Michel M.P.J. Reijnen, Arnhem (NL)

(73) Assignee: Bentley InnoMed GmbH, Hechingen (DE)

( * ) Notice: Subject to any disclaimer, the term of this patent is extended or adjusted under 35 U.S.C. 154(b) by 1000 days.

(21) Appl. No.: 17/790,672

(22) PCT Filed: Jan. 27, 2021

(86) PCT No.: PCT/EP2021/051854
§ 371 (c)(1),
(2) Date: Jul. 1, 2022

(87) PCT Pub. No.: WO2021/151939
PCT Pub. Date: Aug. 5, 2021

(65) Prior Publication Data

US 2023/0045493 A1 Feb. 9, 2023

(30) Foreign Application Priority Data

Jan. 31, 2020 (EP) .................................... 20154952

(51) Int. Cl.
*A61F 2/954* (2013.01)
*A61F 2/852* (2013.01)
(Continued)

(52) U.S. Cl.
CPC .............. *A61F 2/954* (2013.01); *A61F 2/852* (2013.01); *A61F 2/958* (2013.01); *A61M 2025/1045* (2013.01)

(58) Field of Classification Search
CPC .......... A61F 2/852; A61F 2/954; A61F 2/958; A61F 2002/826
See application file for complete search history.

(56) References Cited

U.S. PATENT DOCUMENTS 5,749,825 A 5/1998 Fischell et al.
2005/0182473 A1* 8/2005 Eidenschink .......... A61F 2/958 623/1.11

(Continued)

FOREIGN PATENT DOCUMENTS

CA 3004821 A1 5/2017
EP 1547546 A2 6/2005

(Continued)

OTHER PUBLICATIONS

PCT International Search Report issued May 6, 2021 in connection with PCT/EP2021/051854.

(Continued)

*Primary Examiner* — Sarah W Aleman
(74) *Attorney, Agent, or Firm* — Brooks Kushman P.C.

(57) ABSTRACT

The invention relates to a medical device, the medical device comprising a balloon catheter, a first stent, and a second stent; the balloon catheter having a shaft and an inflatable balloon mounted to the shaft at the distal end the balloon having a distal portion having a first outer diameter and a proximal portion having a second outer diameter, wherein the first diameter is smaller than the second diameter and a transition region located between the distal portion and the proximal portion, a first stent having a first nominal diameter mounted on the distal portion of the balloon and a second stent having a second nominal diameter mounted on the proximal portion of the balloon, a distal portion of the second stent overlapping a proximal portion of the first stent, wherein the proximal end of the first stent is positioned proximal to the distal end of the second stent, the medical device further comprising a pre-cannulation means providing a passage from the interior of the second stent to the exterior of the first stent passing the stent overlapping (Continued)

portion between the inner surface of the second stent and the outer surface of the first stent.

9 Claims, 6 Drawing Sheets

(51) Int. Cl.
*A61F 2/958* (2013.01)
*A61M 25/10* (2013.01)

(56) References Cited

U.S. PATENT DOCUMENTS

2005/0192656 A1* 9/2005 Eidenschink ........... A61F 2/958 623/1.11
2005/0222666 A1* 10/2005 Lualdi ..................... A61F 2/958 606/108
2006/0271152 A1* 11/2006 Hilaire ................... A61B 1/041 623/1.11
2006/0287712 A1 12/2006 Eidenschink
2007/0282419 A1 12/2007 Hilaire et al.
2010/0057020 A1* 3/2010 Uretsky .................. A61F 2/954 604/533
2010/0324664 A1 12/2010 Holzer et al.
2015/0051692 A1 2/2015 Teague et al.
2016/0082230 A1* 3/2016 McGhie .................. A61F 2/958 623/1.12
2018/0036111 A1 2/2018 Despalle De Bearn

FOREIGN PATENT DOCUMENTS

WO 0044307 A1 8/2000
WO 2005084130 A2 9/2005
WO 2010123387 A1 10/2010
WO WO-2013033215 A1 * 3/2013 ............. A61F 2/852

OTHER PUBLICATIONS

European Search Report issued Aug. 11, 2020 in connection with European Appl. No. EP 20 15 4952.

* cited by examiner 90
20
3
4
10

90
2
3
4
F
XXXXXX
5

1
300
200
700
2
60
6
4
5
3
31
10
33
100
32
20

BIFURCATED BALLOON EXPANDABLE STENT ASSEMBLY

CROSS-REFERENCE TO RELATED APPLICATIONS

This application is the U.S. national phase of PCT Appln. No. PCT/EP2021/051854 filed Jan. 27, 2021, which claims priority to European Appl. No. 20154952.4 filed Jan. 31, 2020, the disclosures of which are hereby incorporated in their entirety by reference herein.

SUBJECT MATTER OF THE INVENTION

The present invention is directed to a medical device for treatment of lesions in a bifurcated vessel. More specifically, the invention is directed to a bifurcated balloon-expandable stent catheter assembly designed to treat occlusive disease in bifurcations, a stent-assembly to treat occlusive disease in bifurcations and a method for treatment of a bifurcated vessel.

BACKGROUND OF THE INVENTION

Endovascular treatment has become the primary treatment modality for most arterial occlusive disease, also for more complex pathologies. This is related to a lower morbidity of endovascular surgery on one side and the development of dedicated devices and high-quality stents or stent grafts on the other side. The latter have significantly increased technical outcomes and patency rates. Endovascular treatment is widely accepted in the aorto-iliac and femoropopliteal vessels and is becoming increasingly popular in the crural arteries.

Generally, one of the most important limitations of endovascular treatment of occlusive disease is the proximity of side branches with regard to the lesion. This, for example, is one of the reasons that endovascular treatment has not yet conquered the common femoral artery (CFA) due to the proximity of the deep femoral artery (DFA), but this is also true for other areas near bifurcations like the subclavian artery and the crural trifurcation.

Lesions in the CFA often extend into the orifice of both, the superficial femoral artery (SFA) and DFA and the occlusion of one of them is considered to be undesirable. Surgery in the groin is considered to be a straight forward procedure, yet is related to complications, including wound infections and seroma and also secondary procedures may be difficult due to scar formation. The combination of the above emphasize the urge for a dedicated stent for these specific areas. Case series have proven the safety and efficacy of stenting of the CFA in selected patients. The French TECCO trial recently showed that the endovascular treatment of de novo CFA lesions is related to a lower perioperative morbidity and mortality rate whereas clinical, morphological, and hemodynamic outcomes are comparable with surgery at mid-term. This emphasizes the safety and efficacy of endovascular surgery in this area. In this trial both, self-expanding and balloon expandable stents were used, depending on the lesion type.

Self-expandable stents were used to treat several types of lesions without lesion pre-dilatation. In tight stenosis that precluded stent advancement, angioplasty with a 3 to 4 mm balloon was done to allow stent placement. Post-dilatation was mandatory in case of inadequate deployment. In other type of lesions that involved the common femoral bifurcation, balloon-expandable stents were used to treat costal stenosis of SFA and DFA. In case of occlusion of the SFA, this artery was abandoned and self-expandable stent was placed from CFA into the DFA. In other recent trial it was shown that endovascular interventions of the CFA/DFA show a low rate of peri-procedural morbidity and mortality, but was related to a lower one-year patency than historically observed for CDA endarterectomy. Stent use was associated with reinterventions and amputation, again emphasizing the need for dedicated stents for this area. Lesions in the CFA may be heavily calcified and are usually eccentric with a risk on rupture advocating a covered stent design, whereas flexibility is an issue when extending into the external iliac artery.

Anatomically, there are various other areas that would benefit from a dedicated stent design to treat bifurcations with occlusive disease, including the iliac artery bifurcations, the crural trifurcation and the subclavian artery near the orifice of the vertebral artery. Endovascular treatment of extensive aorto-iliac artery occlusive disease, including CERAB (Covered Endovascular Reconstruction of the Aortic Bifurcation), is well-accepted nowadays and balloon-expandable covered stents have proven to be superior to bare metal stents in extensive occlusive disease. If the distal common iliac artery is affected, however, the choices also are limited: One may use one bare metal stent in this area or rely on plain balloon angioplasty only, with a risk of (in-stent) restenosis or alternatively choose to sacrifice the internal iliac artery, with its own risks. For the crural arteries the CREST configuration has been developed, in analogue with CERAB, using three bare stents. A dedicated stent graft for bifurcations would provide all advantages of covered stents, yet preserving side branches.

Known in the art are several devices to treat bifurcated lesions. U.S. Pat. No. 5,749,825 discloses is a stent delivery catheter system including a stent for insertion at a bifurcation, the system comprising a first guide wire adapted to be inserted through a main artery and into a continuation artery of that main artery, a second guide wire adapted to be inserted through the main artery and into a side branch artery of the main artery, a balloon catheter having an inner shaft which has a distal end and also an inflatable balloon, a side branch tube being joined to the balloon, the side branch tube being adapted to be slidingly advanced over the second guide wire. The stent delivery catheter further comprises an expandable stent having a proximal portion and a distal portion and having an open space therebetween through which open space the side branch tube projects in a distal direction, the proximal portion of the side branch tube lying within the proximal portion of the stent and the distal portion of the side branch tube lying outside the distal portion of the stent. WO 00/44307 A1 discloses a stepped balloon for deploying a stent at a as well as a system for delivering a bifurcated stent. The system comprises a catheter having at least a guide wire lumen and an inflation lumen therein; a balloon mounted to the catheter, a stent mounted to the balloon and comprising a first portion with an expanded diameter a second portion with an expanded diameter, the expanded diameter of the first portion being larger than the expanded diameter of the second portion, a radial opening in the stent adapted to pass a guide wire through the stent, the opening located between a distal and a proximal end of the stent. Further, there is a guide wire exit port located between a distal end and a proximal end of the balloon aligned with the stent such that a wire exiting the port will pass through the radial opening in the stent. WO 2013/033215 discloses a stent arrangement for treating diseased bifurcations. The stent arrangement comprises 3 stents, a proximal stent having a bigger diameter, a distal stent with a smaller diameter than the proximal stent and a third stent extending into the side branch. The stents are delivered employing the kissing balloon technique. US 2007/0282419 discloses a catheter system for stenting bifurcated vessels with a preferably stepped balloon as well as a two-part stent. The two-part stent has a proximal part of a first diameter and a distal part of a second smaller diameter and a non-linked (but overlapping) zone between the proximal part and the distal part. Another stent delivery device for treating bifurcation lesions is disclosed in WO 2005/084130. This stent delivery device for treating bifurcation lesions includes a stepped balloon as well as a proximal stent having a first diameter and a distal stent having a second diameter which is smaller than the first diameter. WO 2010/123387 discloses a stent for treating bifurcation lesions consisting of a distal part that has a smaller diameter and of a proximal part that has a greater diameter, connected with connecting struts to form a cell of the stent of an increased surface area.

However, all these devices still have different draw backs in terms of deliverability, blood flow or strength.

There is still a need for a device for treatment of lesions in the SFA, CFA, DFA or crural arteries that is able to preserve flow both through the main downstream artery as well as the side branch, which has a radial strength high enough to overcome calcified lesions, yet, the stent should be flexible while still resistant to fracture. Also, there should be a diameter difference between the inflow and outflow vessel. There is a continued need for a low-profile device having enough flexibility and tractability to pass curvatures in the vessels during delivery.

SUMMARY OF THE INVENTION

The invention is directed to a medical device, the medical device comprising a balloon catheter, a first stent, and a second stent. The balloon catheter has a shaft and an inflatable balloon mounted to the shaft at the distal end, the balloon has a distal portion having a first outer diameter and a proximal portion having a second outer diameter, wherein the first diameter is smaller than the second diameter and a transition region is located between the distal portion and the proximal portion of the balloon. A first stent having a first nominal diameter is mounted on the distal portion of the balloon and a second stent having a second nominal diameter is mounted on the proximal portion of the balloon. A distal portion of the second stent overlaps a proximal portion of the first stent, wherein the proximal end of the first stent is positioned proximal to the distal end of the second stent. The medical device further comprises a pre-cannulation means providing a passage from the interior of the second stent to the exterior of the first stent passing the stent overlapping portion between the inner surface of the second stent and the outer surface of the first stent.

The invention is further directed to a kit comprising the medical device as described above and a second balloon catheter carrying a third stent.

The invention is further directed to a stent assembly of three stents for stenting a bifurcated vessel, the stent assembly comprising a first stent having a first diameter, a second stent having a second diameter, the second diameter being greater than the first diameter, and a third stent having a third diameter, the third diameter being smaller than the second diameter, wherein the first and third stent are arranged in parallel to each other and wherein a distal portion of the second stent overlaps both, a proximal portion of the first stent and a proximal portion of the third stent.

The invention is further directed to a method for treatment of a bifurcated vessel. In a preferred embodiment, the method of the present invention is directed to a treatment of a lesion in the region of the bifurcation of the common femoral artery (CFA), deep femoral artery (DFA), and superficial femoral artery (SFA).

The accompanying drawings, which are incorporated in and constitute part of this specification, are included to illustrate and provide a further understanding of the product and method of the invention. Together with the description, the drawings serve to explain the principles of the invention.

BRIEF DESCRIPTION OF THE DRAWINGS

FIG. 1 is a schematic view of a medical device in accordance with the invention;

FIG. 6 is an illustration of an alternative embodiment of the balloon of the medical device with a pre-cannulation means fixed thereto;

DETAILED DESCRIPTION OF THE INVENTION

Figure 2:
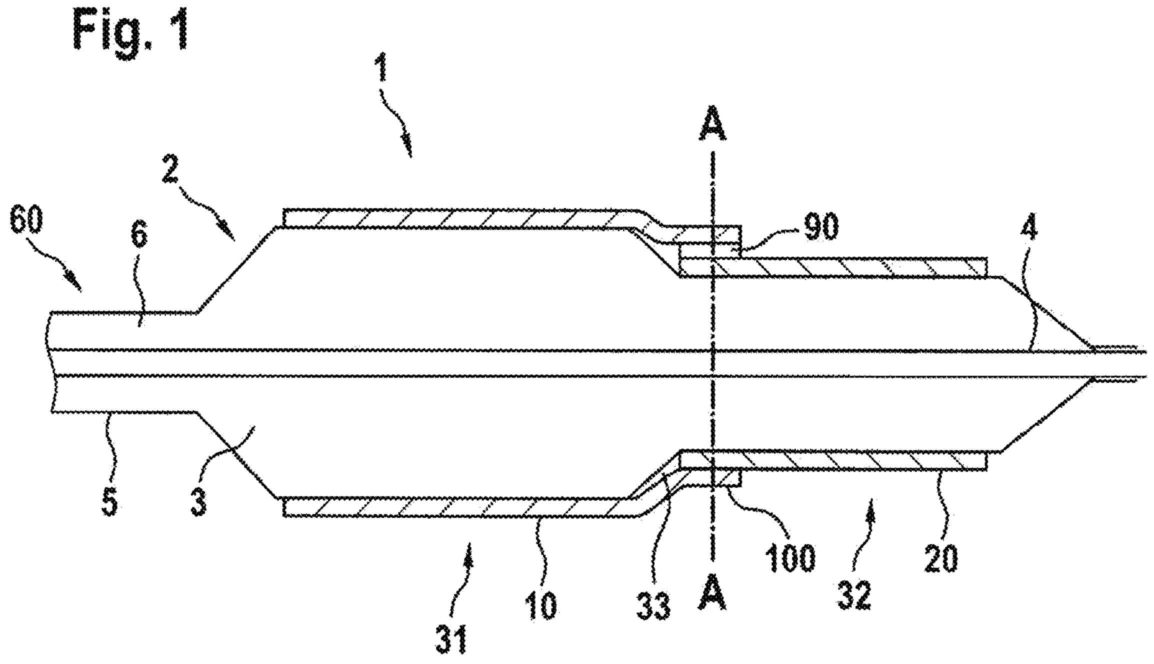
FIG. 2 is a cross-sectional view taken along lines A-A in FIG. 1.

In accordance with the present invention a medical device for treatment of lesions in a bifurcated vessel is provided.

The bifurcated balloon-expandable stent assembly is designed to treat occlusive disease in bifurcations.

There are two options to achieve the above-mentioned goals. In a first embodiment, the bifurcated stent disclosed consists of 3 stents that are interconnected. The first and second stents are arranged subsequently along a longitudinal axis of the stents with the proximal end of the first stent overlapping the distal end of the second stent. This first and second stent arrangement is further pre-cannulated for fenestration in the overlap zone to receive a third stent which branches off the overlapping zone.

In an alternative embodiment, there is provided a first single stent for crossing the bifurcation, the stent being molded tapered to be adapted to the larger vessel diameter of the main branch of a bifurcated vessel proximal to the bifurcation and a stent diameter smaller than the proximal diameter distal of the bifurcation. Further, the stent comprises a fenestration in the distal portion of the proximal larger diameter portion of the stent, which is adapted to receive a second stent for stenting the side branch of the bifurcated vessel.

Further, it is disclosed a 2-step balloon carrying the first single stent and a pre-cannulation port or wire crossing the fenestration.

Also, a method of treatment of occlusive disease of arterial bifurcations employing the 3-stent assembly is disclosed.

Reference will now be made in detail to the present preferred embodiments of the invention, examples of which are illustrated in the accompanying drawings. The method and corresponding steps of the invention will be described in conjunction with the detailed description of the intravascular stent delivery catheter device.

As shown in FIG. 1 the medical device 1 according to the present invention generally includes an elongated catheter shaft 60 having a proximal end and a distal end and an expandable member 3 located proximate the distal end of the catheter shaft. Two expandable stents 10, 20 are mounted on the expandable member 3.

The general principle of catheter assemblies, particularly dilatation balloon catheters, are well known in the art. The elongated catheter is sized and configured for delivery through a tortuous anatomy. For purpose of illustration only, the catheter shaft 60 embodied herein comprises an outer tubular member 5 and an inner tubular member 4. The inner tubular member 4 defines the guidewire lumen for a guidewire (not shown). The catheter can be configured in an over-the-wire (OTW) configuration or the guidewire lumen can be configured for rapid-exchange (RX) delivery, as is well known in the art.

Between the outer tubular member 5 and the inner tubular member 4 an inflation lumen 6 extending between the proximal end portion and the distal end portion of the catheter shaft 60 is defined. Specifically, the coaxial relationship between the inner tubular member 4 and the outer tubular member 5 defines an annular inflation lumen 6 therebetween. The expandable member 3 is provided in fluid communication with the inflation lumen 6. The inflation lumen 6 can supply fluid under pressure to expand the expandable member 3 to a deployed condition, and if desired establish negative pressure to deflate the expandable member 3. The expandable member 3 can thus be inflated and deflated using the inflation lumen 6. Suitable materials and techniques are well known for construction of the catheter shaft.

In further detail, FIG. 1 shows one embodiment of the medical device according to the present invention. It is shown a medical device 1, the medical device comprising a balloon catheter 2, a first stent 20, and a second stent 10; the balloon catheter having a shaft 60 and an inflatable balloon 3 mounted to the shaft at the distal end; the balloon having a distal portion 32 having a first outer diameter and a proximal portion 31 having a second outer diameter, wherein the first diameter is smaller than the second diameter and a transition region 33 located between the distal portion 32 and the proximal portion 31, a first stent 20 having a first nominal diameter mounted on the distal portion of the balloon 32 and a second stent 10 having a second nominal diameter mounted on the proximal portion of the balloon 31, wherein the nominal diameter of the first stent is smaller than the nominal diameter of the second stent, and a distal portion of the second stent overlapping a proximal portion of the first stent, wherein the proximal end of the first stent 20 is positioned proximal to the distal end of the second stent 10. By this configuration a stent overlapping zone 100 is created.

The medical device further comprises a pre-cannulation means 90 providing a passage from the interior of the second stent to the exterior of the first stent passing the stent overlapping portion 100 between the inner surface of the second stent 10 and the outer surface of the first stent 20.

This is further also shown in FIG. 2, which is a cross sectional view of the catheter depicted in FIG. 1 along lines A-A in the overlapping zone 100. As can be seen in this figure, the first stent 20 is mounted on the distal portion of the balloon 3, the distal portion of the second stent 10 is disposed over the proximal portion of the first stent and a pre-cannulation means 90 is disposed between first and second stent.

In the embodiment depicted in FIG. 1 of the medical device 1 a proximal end of the first stent is positioned at the distal end of the transition region 33 of the balloon.

Figure 4:
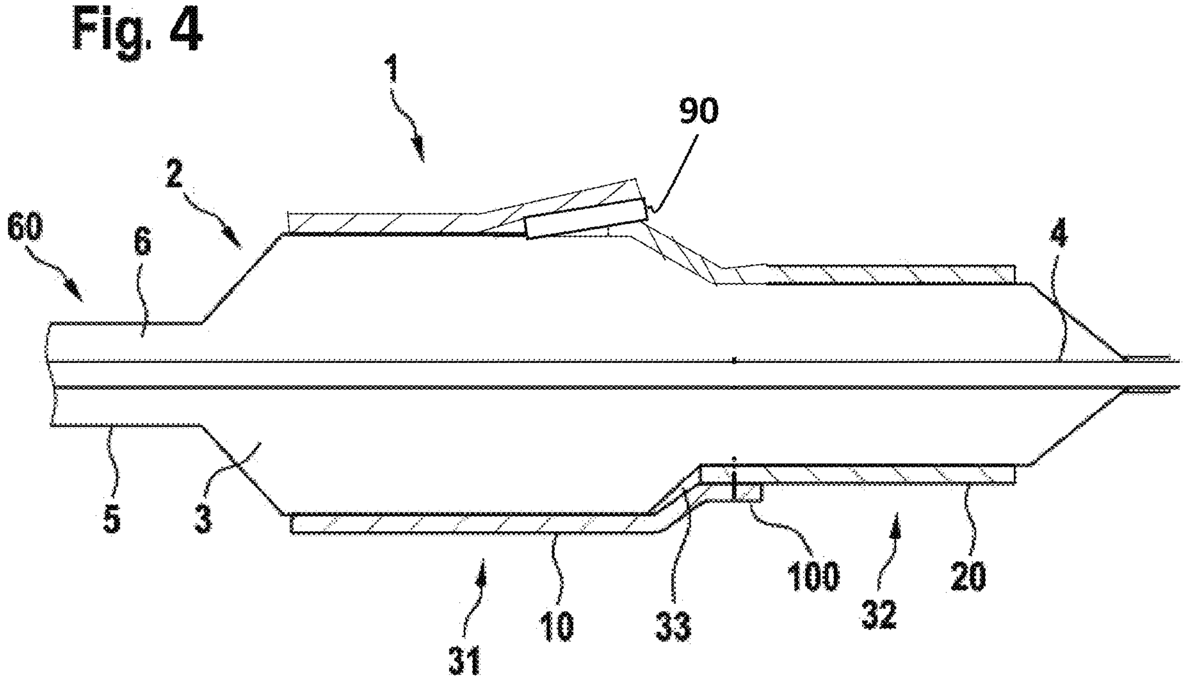
FIG. 4 is a schematic view of an alternative embodiment of the medical device in accordance with the invention.

In a preferred embodiment of the medical device 1 as depicted in FIG. 4, a proximal end of the first stent 20 is positioned at the proximal end of the transition region 33 of the balloon. This assures proper alignment of the stent assembly within the bifurcated vessel.

To further improve the blood flow and avoid bulky accumulation of material within the bifurcation, it is preferred to provide a medical device as depicted above, wherein the wall thickness of the distal portion of the second stent overlapping the proximal portion of the first stent is reduced compared to the wall thickness of the portion of the second stent not overlapping the first stent. Alternatively, or additionally, in a further preferred embodiment of the present invention the wall thickness of the proximal portion of the first stent overlapping the distal portion of the second stent is reduced compared to a wall thickness of the portion of the first stent not overlapping the second stent.

In order to allow either the opening of the second stent at the bifurcation or the insertion of a third stent covering or supporting the second leg of the bifurcation it is important to provide a passage from the interior of the second stent 10 to the exterior of the first stent 20 passing the stent overlapping portion between the inner surface of the second stent and the outer surface of the first stent. This is accomplished by pre-cannulation means 90.

In one embodiment, a guide wire is provided crossing the stent overlapping zone. In view of the fact however, that expansion of the stent will most likely compress also the passage between the stents, there remains some risk that the guide wire is stuck between the overlapping stents and a catheter cannot be advanced over the guide wire and cross the passage due to the tight gap left in between the stents. Accordingly, in a preferred embodiment, the cannulation means 90 is an expandable tube. In this embodiment, a second guide wire will be preloaded into the tube. Once the stent assembly of first and second stent is delivered, i.e. positioned and expanded at the bifurcation of the vessel, a second balloon catheter carrying a third stent will be loaded over the second guide wire, the second balloon catheter carrying a third stent will be advanced over the guidewire until a proximal portion of the third stent will overlap a distal portion of the second stent and the second balloon will be expanded, simultaneously expanding the third stent and the pre-cannulation tube as well as the distal portion of the second stent to provide an opening of the stent assembly into the second leg of the bifurcation. In this embodiment the expandable tube will remain trapped in-between the second stent and the third stent once the stenting procedure is finalized.

Figure 5:
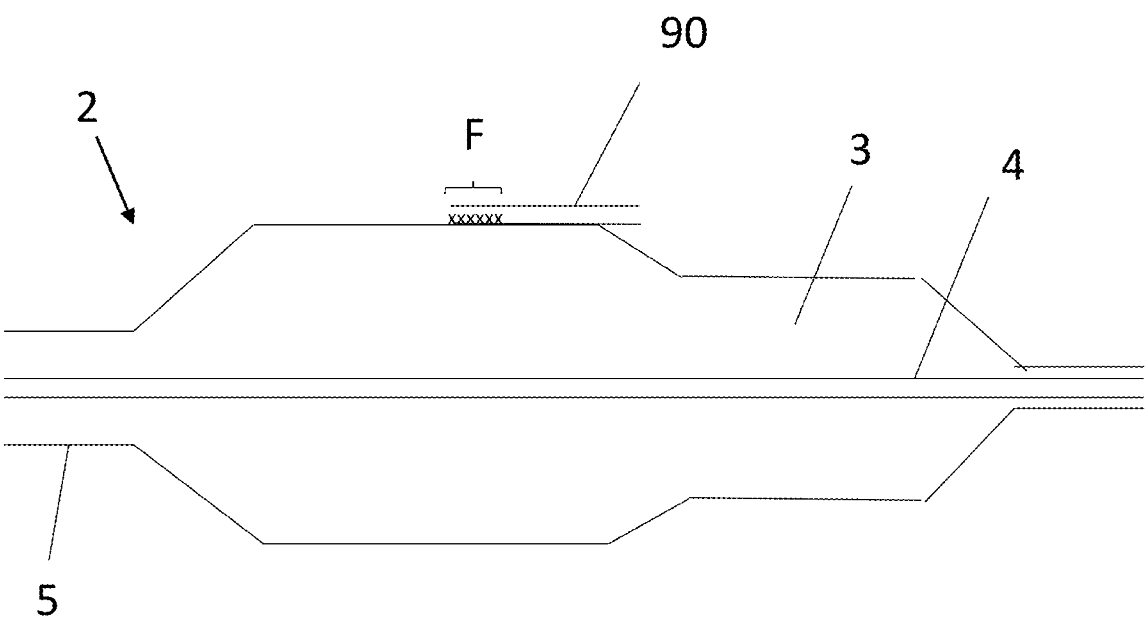
FIG. 5 is an illustration of the balloon of the medical device with a pre-cannulation means fixed thereto.
Figure 6:
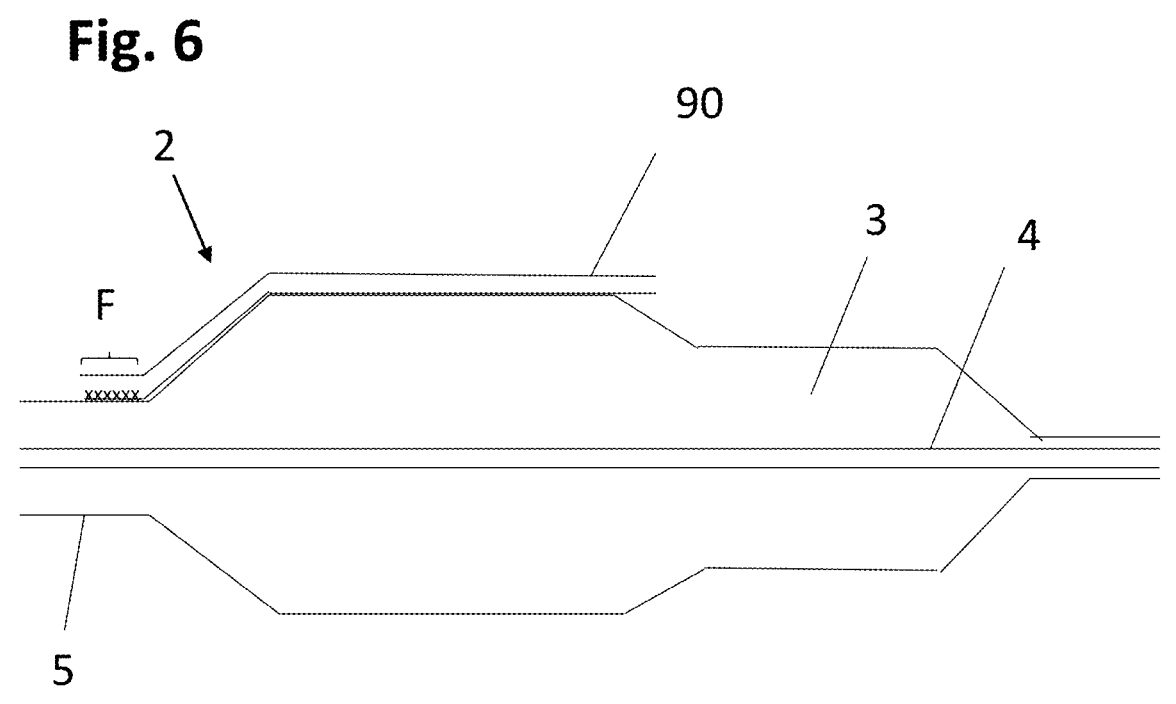

In another embodiment of the present invention as depicted in FIGS. 5 and 6 the pre-cannulation means 90 is a short tube or rod which is connected to the balloon catheter 2 at at least one portion proximal of the region of stent overlap. FIG. 5 depicts a first embodiment of the balloon catheter 2 with the pre-cannulation tube 90 being fixed to the balloon catheter at one portion F proximal of the region of stent overlap. In this embodiment the pre-cannulation tube 90 is affixed at its proximal end to the balloon 3 of the balloon catheter. FIG. 6 illustrates another embodiment of the balloon catheter 2 with the pre-cannulation tube 90 being fixed to the balloon catheter 2 at one portion F proximal of the region of stent overlap where the proximal portion of the pre-cannulation tube 90 is affixed to the outer tubular member 5 of the balloon catheter. The tube or rod remains between the first and the second stent during expansion and placement of the stent assembly in the vessel, thereby serving as a place holder to allow a little gap or passage between the stents once the balloon catheter is retracted from the vessel upon deployment of the stent assembly. In a next step, a guide wire can be placed across the stent passage. Alternatively, the guide wire can already be placed across the passage through the tube while the catheter is still in the vessel. In this embodiment, the guide wire stays in place once the balloon is retracted.

Figure 7:
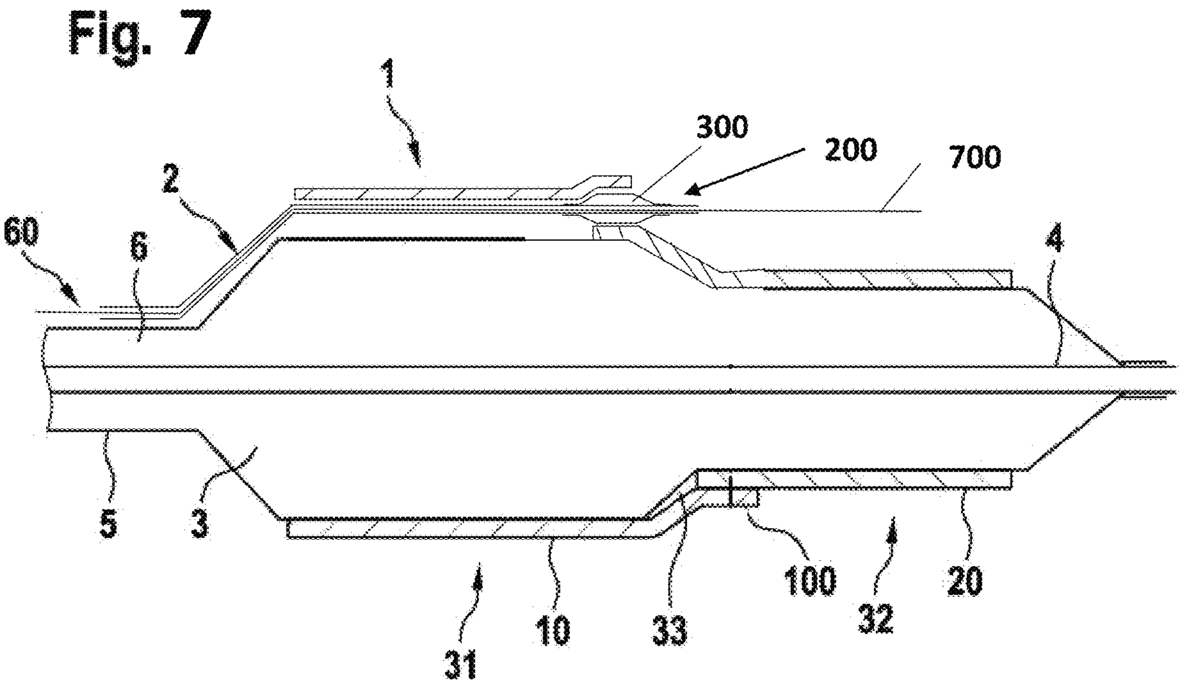
FIG. 7 is a schematic view of an alternative embodiment of the medical device in accordance with the invention.

In a further alternative embodiment illustrated in FIG. 7, the pre-cannulation means 90 is a supplementary balloon catheter 200 with a supplementary balloon 300 positioned between the first and second stent (10, 20) and being inflatable separately from the balloon catheter. This supplementary balloon catheter may be also be preloaded on a second guide wire 700.

Once the stent assembly of first and second stent overlapping is delivered, the passage across the stent overlap can be widened by expanding the supplementary balloon 300 upon expansion of the stents and deflation of the balloon of the medical device to allow crossing the passage with a second balloon catheter carrying a third stent.

The stents of the medical device of the present inventions can be bare metal balloon expandable stents or even preferred at least one of the first or second stent is at least partially covered with a membrane.

In the present application there is further provided a kit comprising the medical as depicted in any of the embodiments described above and a second balloon catheter carrying a third stent.

In a further embodiment, also this third stent can be at least partially covered. In a most preferred embodiment all three stents are covered with a membrane to allow full coverage of all lesions in the bifurcation to be treated.

Figure 3:
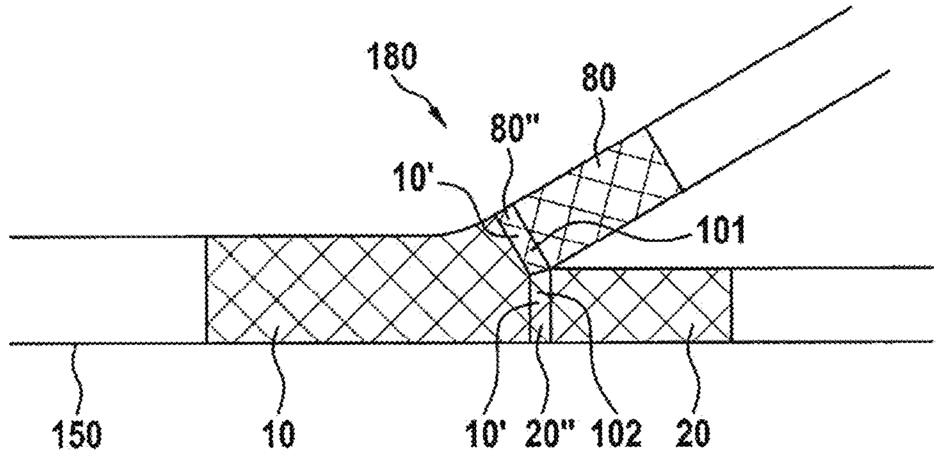
FIG. 3 is a schematic view of a stent assembly in accordance with the present invention.

In a further aspect of the present invention there is disclosed a stent assembly of three stents for stenting a bifurcation. As depicted in FIG. 3, the stent assembly 180 comprises a first stent 20 having a first diameter, a second stent 10 having a second diameter, the second diameter being greater than the first diameter, and a third stent 80 having a third diameter, the third diameter being smaller than the second diameter, wherein the first and third stent are arranged in parallel to each other and wherein a distal portion of the second stent 10' overlaps both, a proximal portion 20" of the first stent and a proximal portion 80" of the third stent. The stent assembly 180 depicted in FIG. 3 is shown in its delivered stat implanted into a bifurcated vessel 150. The overlapping zone of the first and second stent 100 and the overlapping zone of the third and the second stent are located side by side and proximal of the crotch of the bifurcation.

In a preferred embodiment of the present invention a wall thickness of the distal portion of the second stent overlapping the proximal portion of the first stent and/or the third stent is reduced compared to a wall thickness of the portion of the second stent not overlapping the first stent.

In a further preferred embodiment, the wall-thickness the proximal portion of the first and/or third stent overlapping the distal portion of the second stent is reduced compared to a wall thickness of the portion of the first and/or third stent not overlapping the second stent.

As already disclosed above, any of this first, second and third stent can be covered at least partially by a membrane or can be fully covered by a membrane.

In the present invention it is also disclosed a method for treatment of a bifurcated vessel, the method comprising the steps of (a) inserting the medical device according to claim 1 into a bifurcated blood vessel including a main branch dividing in a first side branch and a second side branch creating a crotch, (b) advancing the medical device within the main branch of the bifurcated vessel to a position where the distal end of the second stent is aligned with the crotch of the bifurcation; (c) deploying the first and the second stent simultaneously by inflating the balloon; (d) retracting the balloon catheter; (e) inserting a second balloon catheter carrying a third balloon expandable stent on an expandable balloon into the bifurcated vessel; (f) advancing the second balloon within the main branch of the bifurcated vessel and across the passage from the interior of the second stent to the exterior of the first stent passing the stent overlapping portion between the inner surface of the second stent and the outer surface of the first stent into the second side branch of the bifurcation site until the proximal end of the third stent is aligned to the proximal end of the first stent and overlapping a proximal portion of the second stent; (f) deploying the third stent within the second side branch of the bifurcated vessel by inflating the balloon of the second balloon catheter, thereby opening the pre-cannulation between the first stent and the second stent; (g) retracting the second balloon catheter.

In a preferred embodiment, the method further comprises the steps of (h) placing a first guidewire through the main branch into the first side branch of the bifurcated vessel, (i) placing a second guidewire through the main branch into the second side branch of the bifurcated vessel, (k) placing the first balloon catheter over the first wire with the second wire being placed into the pre-cannulation means and (l) advancing the first balloon catheter over both wires to the bifurcation site.

In an alternative embodiment it is disclosed a method for treatment of a bifurcated vessel, the method comprising the steps of (a) placing a first guidewire through the main branch into the first side branch of a bifurcated vessel, the bifurcated vessel including a main branch dividing in a first side branch and a second side branch creating a crotch, (b) placing a second guidewire through the main branch into the second side branch of the bifurcated vessel, (c) placing the first balloon catheter over the first wire, (d) placing the supplementary balloon catheter over the second wire and advancing the first balloon catheter and the supplementary balloon catheter over both wires to the bifurcation site; (e) advancing the medical device within the main branch of the bifurcated vessel to a position where the distal end of the second stent is aligned with the crotch of the bifurcation; (f) deploying the first and the second stent simultaneously by inflating the balloon; (g) retracting the balloon catheter; (h) inflating the supplementary balloon within the passage from the interior of the second stent to the exterior of the first stent to enlarge the passage; (i) retracting the supplementary balloon catheter; (k) inserting a second balloon catheter carrying a third balloon expandable stent on an expandable balloon over the second guidewire crossing the bifurcation and reaching into the second leg; (l) advancing the second balloon catheter within the main branch of the bifurcated vessel and across the passage from the interior of the second stent to the exterior of the first stent passing the stent overlapping portion between the inner surface of the second stent and the outer surface of the first stent into the second side branch of the bifurcation site until the proximal end of the third stent is aligned to the proximal end of the first stent and overlapping a proximal portion of the second stent; (m) deploying the third stent within the second side branch of the bifurcated vessel by inflating the balloon of the second balloon catheter, thereby opening the pre-cannulation between the first stent and the second stent; (n) retracting the second balloon catheter.

In a preferred embodiment the method further comprising the step of (o) retracting the guidewires.

The method as depicted above is generally suitable for treatment of any bifurcated vessel throughout the body. However, this method is particularly suitable to treat lesions in peripheral bifurcation sites, like the bifurcation of CFA, SFA and DFA.

Further possible treatment sites include the subclavian artery, the celiac trunk and the distal popliteal artery or crural trifurcation. Also, a large diameter version results in a two-piece dedicated CERAB stent that further optimizes the geometry of the reconstruction. The stent can also be used for (pseudo) aneurysms.

EXAMPLES

In one example the system consists of three parts that are interconnected. The first part consists of two balloon expandable covered stents that are located on a single balloon. The two stents have a minimal overlap on the balloon (3 to 5 mm). A balloon is chosen with the option to expand into two sizes or alternatively a balloon appropriate for the outflow vessel is used and exchanges for a larger one for the proximal part. An important feature is the pre-cannulation of the overlap zone, already on the balloon, in order to create a fenestration to the side branch using a smaller sized balloon. This will subsequently be stented as the last phase of the procedure.

In another example of the present invention the system consists of two parts that are interconnected. First, there is a main part of the configuration consisting of a single balloon expandable stent that extends from the SFA into the proximal CFA or distal AJE. This balloon expandable stent is molded into a tapered stent using two sizes of balloons or alternatively a balloon appropriate for the outflow vessel could be used and exchanged for a larger one for the proximal part. In the larger part of the stent is a fenestration created. That is pre-cannulated and aligned with the side branch, used to place an additional balloon expandable covered stent into this side branch. Due to the occlusive disease flaring does not seem to be necessary, but can be performed. The fenestration should be marked clearly and the location should be visible in the uninflated situation for proper alignment.

The contralateral CFA is punctured and an introducer sheath is placed. A guidewire is positioned over the aortic bifurcation into the external iliac artery of the diseased side and subsequently, a long sheath is positioned in the distal external iliac artery (or the common iliac artery in case the iliac bifurcation would be treated). Then two wires are introduced. The first (0.35) wire is positioned into the SFA, when necessary partly in the subintimal plane in case of an occluded SFA. A second (0.18) stiff wire is positioned in the DFA. Then, the "two stent balloon" is located onto both wires and positioned with the pre-cannulation catheter aligned with the orifice of the DFA. Then, the balloon is inflated and the stent expanded to the nominal diameter of the SFA. Then the DFA wire is loaded with the second balloon (typically a 4-5 mm) and inflated, creating a space for the third balloon expandable stent. Simultaneously the stent that is in the CFA is further expanded to achieve proper apposition in the CFA, yet remaining the created fenestration open. Then the DFA is stented using a balloon expandable covered stent over the 0.18 wire, with optional flaring.

Typically, the diameter of the part in the SFA is 5-7 mm, while the part in the CFA is between 8-10 mm. The length in the SFA can be standardized (2-3 cm) as it can be extended distally by any commercially available stent (graft). Proximally, the stent should cover the entire diseased segment. Often, this will mean that the stent will start in the distal external iliac artery, emphasizing the need for flexibility. The covered stent in the DFA typically has a diameter of 5-6 mm and the length is between 8-12 mm. In case the common iliac artery is treated, the needed diameters are commonly between 7-10 mm for the common iliac artery, 7-8 mm for the external iliac artery and 5-7 mm for the internal iliac artery. Obviously, for the below the knee arteries smaller diameters would be required.

As the vascular patients regularly require additional procedures, either endovascular or cardiac, the groin may be needed for access. Therefore, the graft material is chosen in such a way the it is possible to puncture the stent graft safely without damaging the stent or covering material.

By means of example the CFA is chosen for description of the procedure, but a similar technique can be used in the mentioned other areas.

In one example the contralateral CFA is punctured and an introducer sheath is placed. A guidewire is positioned over the aortic bifurcation into the external iliac artery of the diseased side and subsequently, a long sheath is positioned in the distal external iliac artery (or the common iliac artery in case the iliac bifurcation would be treated). Then two wires are introduced. The first (0.35) wire is positioned into the SFA, when necessary partly in the subintimal plane in case of an occluded SFA. A second (0.18) stiff wire is positioned in the DFA. Then, the "two stent balloon" is located onto both wires and positioned with the pre-cannulation catheter aligned with the orifice of the DFA. Then, the balloon is inflated and the stent expanded to the nominal diameter of the SFA. Then the DFA wire is loaded with the second balloon (typically a 4-5 mm) and inflated, creating a space for the third balloon expandable stent. Simultaneously the stent that is in the CFA is further expanded to achieve proper apposition in the CFA, yet remaining the treated fenestration open. Then the DFA is stented using a balloon expandable covered stent over the 0.18 wire, with optional flaring.

In another example access is similar to the access described above. The bifurcation stent is loaded onto both wires and positioned properly with the fenestration aligned with the orifice of the DFA. Then the stent is inflated to the diameter of the SFA and subsequently the proximal part of the stent, located in the CFA, is further expanded to achieve proper apposition in the common iliac artery. Subsequently the second stent graft is inserted in the DFA over the second wire, positioned in the fenestration and deployed with optional flaring.

The invention claimed is:

1. A medical device, the medical device comprising a balloon catheter, a first stent, and a second stent;

the balloon catheter having a shaft and an inflatable balloon mounted to the shaft at the distal end the balloon having a distal portion having a first outer diameter and a proximal portion having a second outer diameter, wherein the first diameter is smaller than the second diameter and a transition region located between the distal portion and the proximal portion, a first stent having a first nominal diameter mounted on the distal portion of the balloon and a second stent having a second nominal diameter mounted on the proximal portion of the balloon, a distal portion of the second stent overlapping a proximal portion of the first stent, wherein the proximal end of the first stent is positioned proximal to the distal end of the second stent, the medical device further comprising a pre-cannulation means providing a passage from the interior of the second stent to the exterior of the first stent passing the stent overlapping portion between the inner surface of the second stent and the outer surface of the first stent.

2. A medical device according to claim 1, the medical device further comprising a pre-cannulation means providing a passage from the interior of the second stent to the exterior of the first stent passing the stent overlapping portion between the inner surface of the second stent and the outer surface of the first stent.

3. A medical device according to claim 1, wherein a proximal end of the first stent is positioned at the proximal end of the transition region of the balloon.

4. A medical device according to claim 1, wherein a wall thickness of the distal portion of the second stent overlapping the proximal portion of the first stent is reduced compared to a wall thickness of the portion of the second stent not overlapping the first stent.

5. A medical device according to claim 1, wherein the pre-cannulation means is an expandable tube.

6. A medical device according to claim 1, wherein the pre-cannulation means is a tube connected to the balloon catheter at at least one portion proximal of the region of stent overlap.

7. A medical device according to claim 1, wherein the pre-cannulation means is a supplementary balloon catheter with a supplementary balloon positioned between the first and second stent and being inflatable separately from the balloon catheter.

8. A medical device according to claim 1, wherein at least one of the first or second stent is at least partially covered with a membrane.

9. A kit comprising the medical device according to claim 1 and a second balloon catheter carrying a third stent.

* * * * *